(12) United States Patent
Berry et al.

(10) Patent No.: US 9,220,731 B2
(45) Date of Patent: Dec. 29, 2015

(54) CONTINUOUS CULTURING DEVICE

(75) Inventors: Eric Berry, Udine (IT); Francesco Curcio, Pagnacco (IT)

(73) Assignee: VIVABIOCELL, S.P.A., Udine (IT)

( * ) Notice: Subject to any disclaimer, the term of this patent is extended or adjusted under 35 U.S.C. 154(b) by 0 days.

(21) Appl. No.: 13/515,685

(22) PCT Filed: Dec. 15, 2010

(86) PCT No.: PCT/EP2010/069768
§ 371 (c)(1),
(2), (4) Date: Oct. 23, 2012

(87) PCT Pub. No.: WO2011/073261
PCT Pub. Date: Jun. 23, 2011

(65) Prior Publication Data
US 2013/0034898 A1    Feb. 7, 2013

(30) Foreign Application Priority Data

Dec. 16, 2009  (EP) ..................................... 09179465

(51) Int. Cl.
| | | |
|---|---|---|
| *C12M 1/00* | (2006.01) | |
| *A61K 35/32* | (2015.01) | |
| *C12M 3/00* | (2006.01) | |
| *C12M 1/12* | (2006.01) | |
| *A61K 9/00* | (2006.01) | |

(52) U.S. Cl.
CPC . *A61K 35/32* (2013.01); *A61K 9/00* (2013.01); *C12M 21/08* (2013.01); *C12M 25/14* (2013.01)

(58) Field of Classification Search
CPC ............ C12M 1/00; C12M 1/04; C12M 1/24; C12M 3/00; C12M 3/02; C12M 3/04; C12M 3/06; C12M 21/08; C12M 25/14; A61K 35/32; A61K 9/00

USPC ....................... 435/289.1, 295.2, 297.2, 297.4
See application file for complete search history.

(56) References Cited

U.S. PATENT DOCUMENTS

| | | | |
|---|---|---|---|
| 3,634,508 A | | 1/1972 | Bream et al. |
| 4,693,983 A | * | 9/1987 | Davies et al. ............. 435/297.1 |

(Continued)

FOREIGN PATENT DOCUMENTS

| | | |
|---|---|---|
| WO | 2005056747 | 6/2005 |
| WO | 2006033935 | 3/2006 |

(Continued)

OTHER PUBLICATIONS

Bream J B et al: "Substituted Phenylacetylguanidines: A New Class of Antihypertensive Agents" Arzneimittel Forschung. Drug Research, ECV Editio Cantor Verlag, Aulendorf, DE, vol. 25, No. 10, Jan. 1, 1975, pp. 1477-1482.

(Continued)

*Primary Examiner* — Nathan Bowers
*Assistant Examiner* — Timothy Barlow
(74) *Attorney, Agent, or Firm* — Lucas & Mercanti LLP

(57) ABSTRACT

A continuous device for culturing mammalian cells in a three-dimensional structure for the transplantation or implantation in vivo is described. The culturing device comprises (a) a scaffold formed by a matrix of interconnected growth surfaces spaced at regular intervals and (b) a fluid distribution means at the inlet and the exit of the growth areas. The device is particularly useful for culturing bone cells for dental implants or bone reconstruction.

16 Claims, 9 Drawing Sheets

(56) References Cited

U.S. PATENT DOCUMENTS

| | | |
|---|---|---|
| 6,194,210 B1 | 2/2001 | Leu et al. |
| 6,218,182 B1 | 4/2001 | Naughton et al. |
| 6,602,878 B1 | 8/2003 | Carniato et al. |
| 2005/0003530 A1* | 1/2005 | Gerlach .................. 435/293.1 |
| 2005/0276791 A1 | 12/2005 | Hansford et al. |
| 2006/0177924 A1 | 8/2006 | Rezania et al. |
| 2009/0041825 A1 | 2/2009 | Kotov et al. |
| 2009/0186412 A1 | 7/2009 | Yamanaka et al. |
| 2009/0317447 A1* | 12/2009 | Hsiao et al. .................. 424/426 |

FOREIGN PATENT DOCUMENTS

| | | |
|---|---|---|
| WO | 2006053291 | 5/2006 |
| WO | 2007146086 A1 | 12/2007 |

OTHER PUBLICATIONS

Clement B et al: "Microsomal catalyzed N-hydroxylation of N-hydroxyguanfacine and reduction of N-hydroxyguanfacine." Archiv Der Pharmazie Oct. 1997 LNKD-Pubmed: 9396389, vol. 330, No. 9-10, Oct. 1997, pp. 303-306.

* cited by examiner

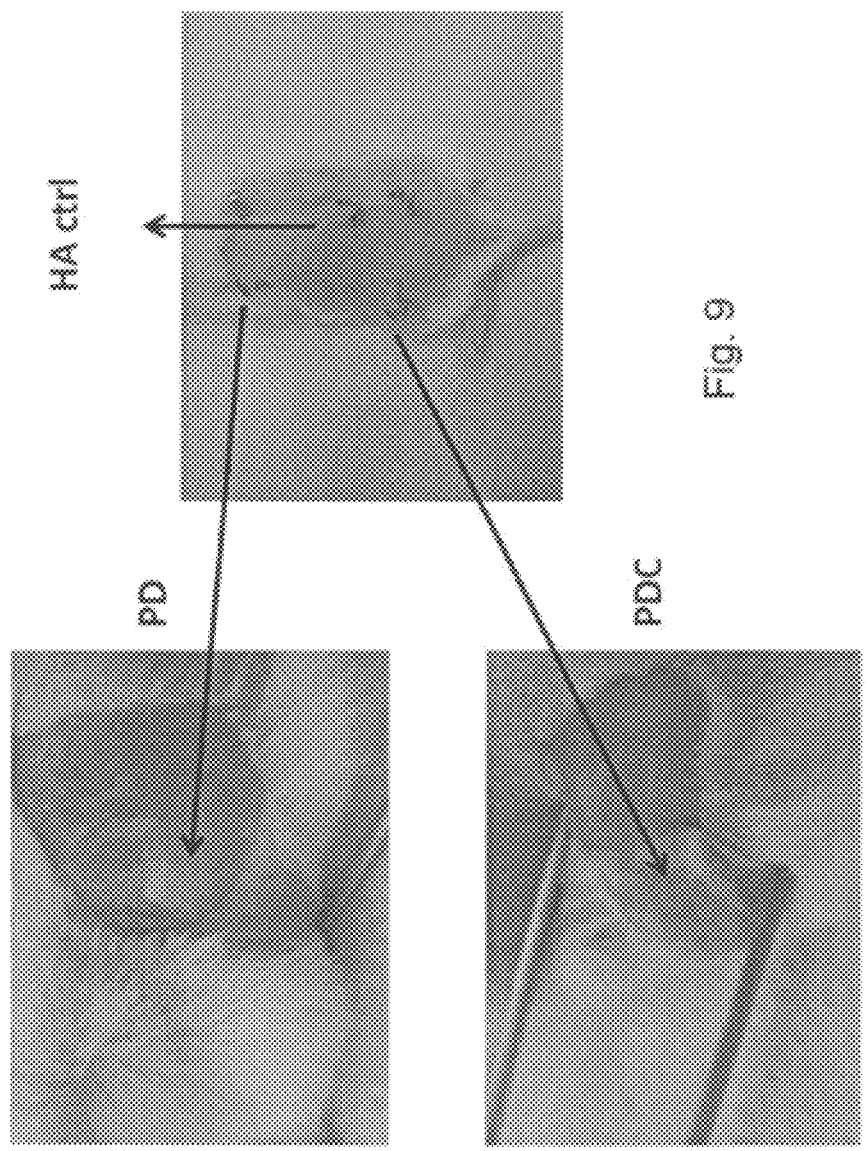

CONTINUOUS CULTURING DEVICE

CROSS-REFERENCE TO RELATED APPLICATIONS

This application is a 371 of PCT/EP2010/069768 filed Dec. 15, 2010, which claims the benefit of European Patent Application No. 09179465.1 filed Dec. 16, 2009, the contents of each of which are incorporated herein by reference.

The present invention relates to a device for culturing mammalian cells in a three-dimensional structure for the transplantation or implantation in vivo. More particularly, the present invention relates to a continuous culturing device for culturing bone cells for dental implants or bone reconstruction.

There is increasing interest in growing cells in three-dimensional (3D) environments such as on a 3D structure or scaffold. Cell culture on 3D scaffolds is useful in tissue engineering for the generation of implantable tissue structures. Intrinsic difficulties with 3D cultures in 3D scaffolds are (i) the uniform and efficient seeding of cells throughout the scaffold pores, and (ii) limited mass transfer to the cells in the central scaffold part.

The past three decades have shown great advances in the area of tissue engineering but the problem associated with the difficulty of culturing cells at the center of deep or thick structures remains.

U.S. Pat. No. 6,194,210 describes a process for hepatitis A virus in an aggregated microcarrier-cell culture.

U.S. Pat. No. 6,218,182 describes a method for culturing 3D tissues, in particular liver tissue for use as an extracorporeal liver assist device, in a bioreactor where cells are seeded and provided with two media flows, each contacting a different side of the cells.

US 2009/0186412 describes a porous cell scaffold and methods for its production. All prior art references address the problems that arise when a culture system with a high density of cells encounters flow irregularities.

Known bioreactors do not efficiently simulate in vivo nutrient mechanism in thick structures or when culture density is high.

Regulation of flow, delivery of nutrients, gasses and removal of waste in the bodies of mammals is an automated process that encompasses many complex functions in the body. Blood is a complex system, that supports the ability to transport large quantities of gasses and nutrients to and from cells throughout the body. Flow is managed by a complex system that automatically alters volume and pressure to redistribute the flow of blood to areas of high demand. The distribution system includes thousands of branches and each branch may have smaller internal diameters until finally arriving at the dimensional level where the cells are nourished. The use of Computational Fluid Dynamics (CFD) software permits analysis of the flow within a complex structure and its container. When a suitable combination of characteristics are identified, the metabolic parameters can be studied to assure that both the utilisation rate of materials and the production of waste products remain in a typically safe zone. One example would be to calculate the maximum cell density and the oxygen consumption rate, to assure that all the cells remain aerobic.

We have now found a continuous culture device which solves the problem of culturing cells at the center of deep or thick structures.

Object of the present invention is a continuous culture device comprising (a) a scaffold formed by a matrix of interconnected growth surfaces spaced at regular intervals and (b) a fluid distribution means at the inlet and the exit of the growth areas.

The spacing and definition are arranged to permit directional flow through and around the growth surfaces uniformly.

The fluid distribution means at the inlet and the exit of the growth areas permits an adequate flow to each growth surfaces. The fluid distribution is analysed using computational fluid dynamics and key metabolite utilisation analysis to assure that the cells are not subject to detrimental growth conditions.

Preferably, the fluid distribution means distributes the incoming flow of fresh nutrients and gasses to the growth surfaces. The cross-sectional area of the distribution device channels and the number of channels can be adjusted to facilitate the uniform distribution to the growth surfaces, depending on the shape of the growth surfaces and the total number of cells supported by the growth surfaces. Preferably, the culture device includes a matrix of interconnected growth surfaces, defined by the interconnection of multiple fibers or three-dimensional structures, in an organized and repetitive manner, which can incorporate any number of facets or surface artefacts utilised to encourage or enhance the attachment and growth of cells.

The three-dimensional structures forming the matrix can be cylindrical, rectangular, hexagonal or any other shape or combination of shapes and the surfaces may be smooth or textured.

In a practical preferred embodiment of the invention, the scaffold is formed by a matrix of interconnected growth surfaces spaced at regular intervals around a central support.

The open spaces formed by the interconnection of the structures, are equal or larger than 0.7 mm and smaller than 3 mm, preferably equal or larger than 0.9 mm and smaller than 3 mm. The spacing in the preferred embodiment is greater than 1.0 mm, but can be altered as required by the need for physical strength of the scaffold. In a still more preferred embodiment of the present invention, the interconnected growth surfaces are spaced at regular intervals equal or larger than 1.0 mm and less than 2.0 mm.

Spacing is a characterizing feature of the present invention. The variability of the parameter around the above range allows to optimize the flow of medium throughout the scaffold and, at the same time, to impart an adequate solidity to the 3D structure for all the devices according to the invention independently from their final shape and dimension. The open spaces formed by the interconnecttion of the growth surfaces create the organised characterizing structure of the device of the present invention which differs from the porous structure of the device known from the prior art.

The shape of the scaffold is preferably cubic but it could be another shape, for example cylindrical or anatomically correct.

Preferably, the culture device includes a large number of interconnected growth surfaces uniformly arranged to create large open areas that limit the maximum number of cells per cubic volume facilitating the easy vascularization of the growth areas.

The culture device can be made of any biocompatible material.

Biocompatible materials are any biocompatible organic polymer or mixture thereof as well as blends or mixtures of biocompatible organic polymers with biocompatible organic or inorganic non-polymeric compounds.

Non limitative specific examples of components of the biocompatible material useful in the present invention are polycaprolacton, polyethylene oxide—terephthalate, polyamide, poly-L-lactic acid, polyglycolic acid, collagen, fibronectin, hydroxyapatite, etc.

In a practical preferred embodiment, the culture device further comprises an aseptically sealed housing that can be disassembled at the completion of the culture period. Said aseptic housing can include a sealed removable cover, an inlet distribution means, an optional exit distribution means, and the necessary support means required to locate and secure the growth surfaces in the culture device.

The housing can be in the form of a rectangle, cylinder or any other shape necessary to hold the culture device and provide additional features for aseptic removal of the scaffold.

The present invention offers several advantages over previous culture devices in that nutrient delivery permits the creation of and maintaining the viability of tissue on a thick (>1 mm) substrate.

The 3D culture device of the present invention can be produced in a single step process.

Alternatively, a 2D layer can be produced first, and then the single 2D layers can be assembled one over the others to form the 3D culture device according to the present invention.

The final dimension of the 3D culture device will depend on the number of assembled 2D layers.

The culture device of the present invention can be efficiently used for culturing any kind of cells into a 3D tissue. Preferably it is used for culturing cells for dental implants or bone reconstruction. Once the cells have grown into a 3D tissue, the media flow may be stopped and the tissue can be used or preserved for future use. The culture device of the present invention can be efficiently used also for culturing cells directly into the body. In fact, the device can be implanted into the patient in need of tissue reconstruction and the culturing is effected in vivo.

By using the culture device according to the present invention cells may be grown in a controlled environment on a biodegradable scaffold. The large open areas formed by the interconnection of the growth surfaces allows them to be exposed to a uniform flow of medium and to prevent fouling during the growth process. In particular, fouling or blockade of the growth surface by gas bubbles during the growth process is prevented.

Moreover, with the culture device of the invention, culture conditions are monitored continuously and any departures from the desired conditions are automatically corrected and alarmed. This provides conditions necessary to maintain cells in their undifferentiated state, to minimise the maximum cell density and the associated toxic necrosis, and to provide an environment that is not diffusion limited for key nutrients and gasses.

Furthermore the culture device according to the present invention provides the growth of tissues also in the absence of cells, as shown in experiments carried out on rabbits.

EXAMPLE

Experimental Protocol

A two-layer scaffold (11 mm×11 mm×5 mm) according to the present invention, cut in four pieces of equal dimension, was used for the cell growth experiment on mice.
Histological Analysis and Results
The four continuous culturing devices were implanted into immunodeficient NOD/SCID mice.

The analysis of the inflammatory reaction after one week from the implantation showed no sign of typical inflammatory reaction, i.e. swelling, redness, exudates, etc.

Histological analysis of the control material HA (Hydroxy Apatite), i.e. a biomedical material commercially available used as standard sample, did not reveal phlogosis (e.g. lymphocytic infiltration) conversely it revealed the integration of the porous ceramic material with the tissues (fibroblast colonization of the material's pores). Poly-capro-lactone was removed from all the samples containing the continuous culturing device object of the present invention and was replaced by paraffin. It resulted in a negative or empty image on microphotographs.

Histological analysis of the samples P (Polycaprolactone), PC (Polycaprolactone with cells), PD (Polycaprolactone with tri-calcium phosphate dipping) (FIG. 7), and PDC (Polycaprolactone with tri-calcium phosphate dipping with cells) (FIG. 8) did not reveal any tissue's inflammatory process. Then the implantation in vivo of the continuous culturing device object of the present invention, provided cell growth without involving tissue's inflammation process.

The analysis carried out on mice demonstrated that the continuous culturing device is biocompatible and not locally toxic. Moreover the characteristic 3D structure of the continuous culturing device provides the tissue's regrowth.

The present invention is now illustrated in more details in the following drawings which represent specific embodiments of the invention without limiting it.

DETAILED DESCRIPTION OF THE DRAWINGS

Figure 1:
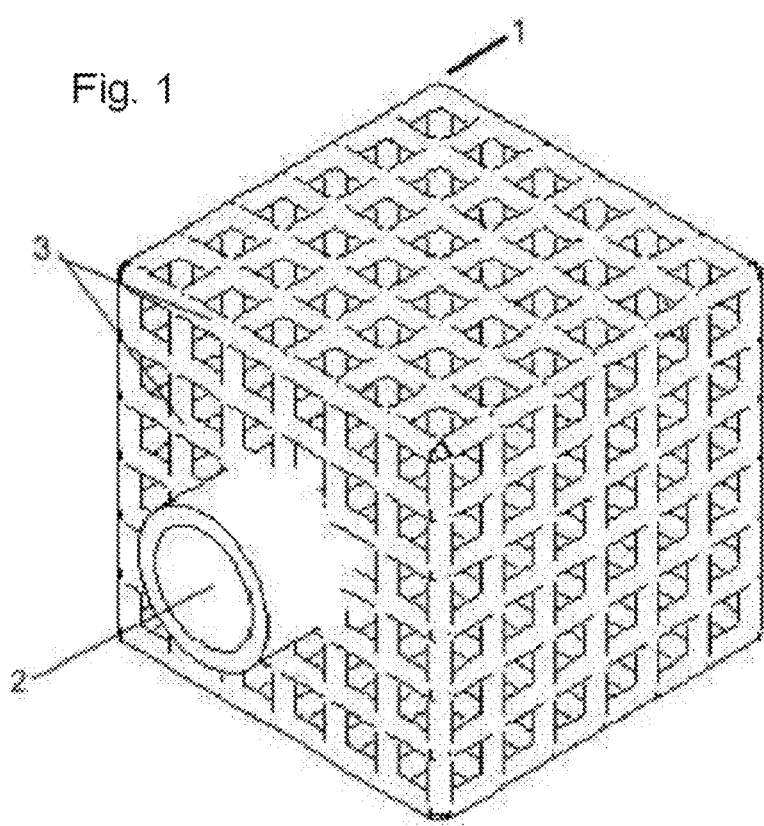
FIG. 1 One embodiment of the scaffold
FIG. 2 One embodiment of a flow distribution device
FIG. 3 One embodiment of scaffold between two flow distribution devices
FIG. 4 System flow chart
FIG. 5 CFD Flow analysis
FIG. 6 Photographic Flow analysis
FIG. 7 Microphotograph of the sample PD
FIG. 8 Microphotograph of the sample PDC
FIG. 9 Photographs of samples HA, PD and PDC

FIG. 1 is one embodiment of the scaffold. Scaffold (1) is formed by the interconnection of a matrix of cylindrical (3) structures. The scaffold (1) is formed around the central support (2).

Figure 2:
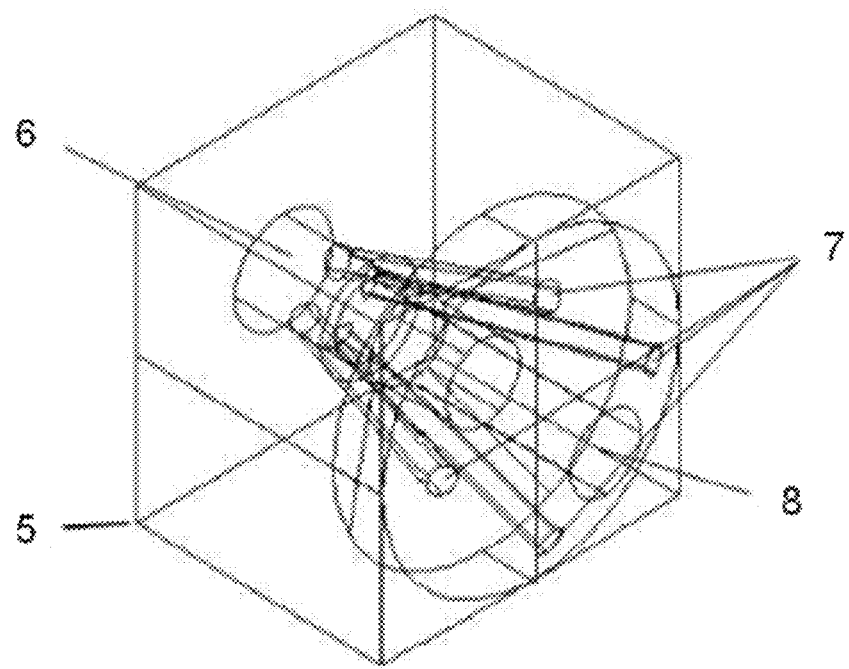

FIG. 2 is one embodiment of the fluid distribution device (5). In this device, the fluid is presented to the device (5) at a common conduit (6) which is connected to the distribution conduits (7). A support means (8) is shown to connect with the central support (2) of the scaffold (1).

Figure 3:
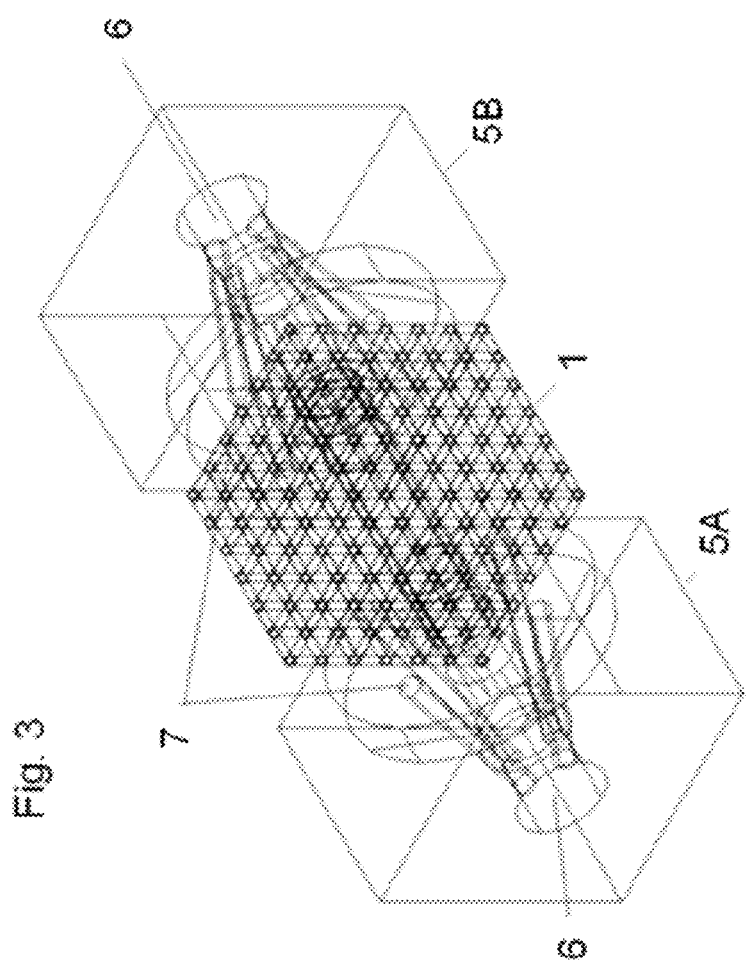

FIG. 3 depicts a scaffold (1) positioned between two of the distribution devices (5). In this embodiment the fluid is delivered to the inlet common conduit (6) and further distribute to distribution conduits (7) and then is distributed through and around the open structures (4) of scaffold (1). The fluid is then collected and presented to common conduits (7), located in the outlet device (5B) where it is collected and presented to the common conduit (6) of the distribution device (5B).

Figure 4:
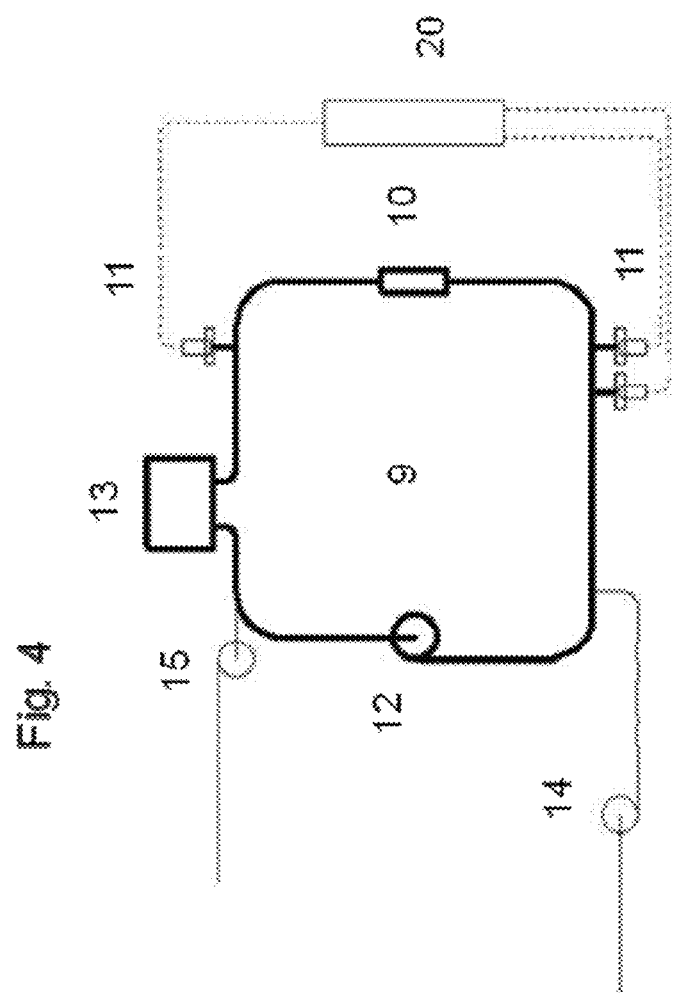

FIG. 4 is an outline view of the culture device (10) connected to a central circulation system (9). When the culture device (10) is connected to system (9), it is positioned to receive a continuous flow of nutrients and dissolved gasses provided by pump (12). A central circulation loop is created by connecting the outlet of pump (12) with the inlet of the culture device (10). The outlet of the culture device (10) is connected with the inlet of pump (12) through the fluid reservoir (13). In constant communication with the fluid in the system (12) are a variety of sensors (11). The sensors (11) are connected with a control means (20) that monitors and controls the conditions of system (12). Additional pumps (14, 15) are provided to supply metered delivery of fresh nutrients to the system, and waste materials from the system.

Figure 5:
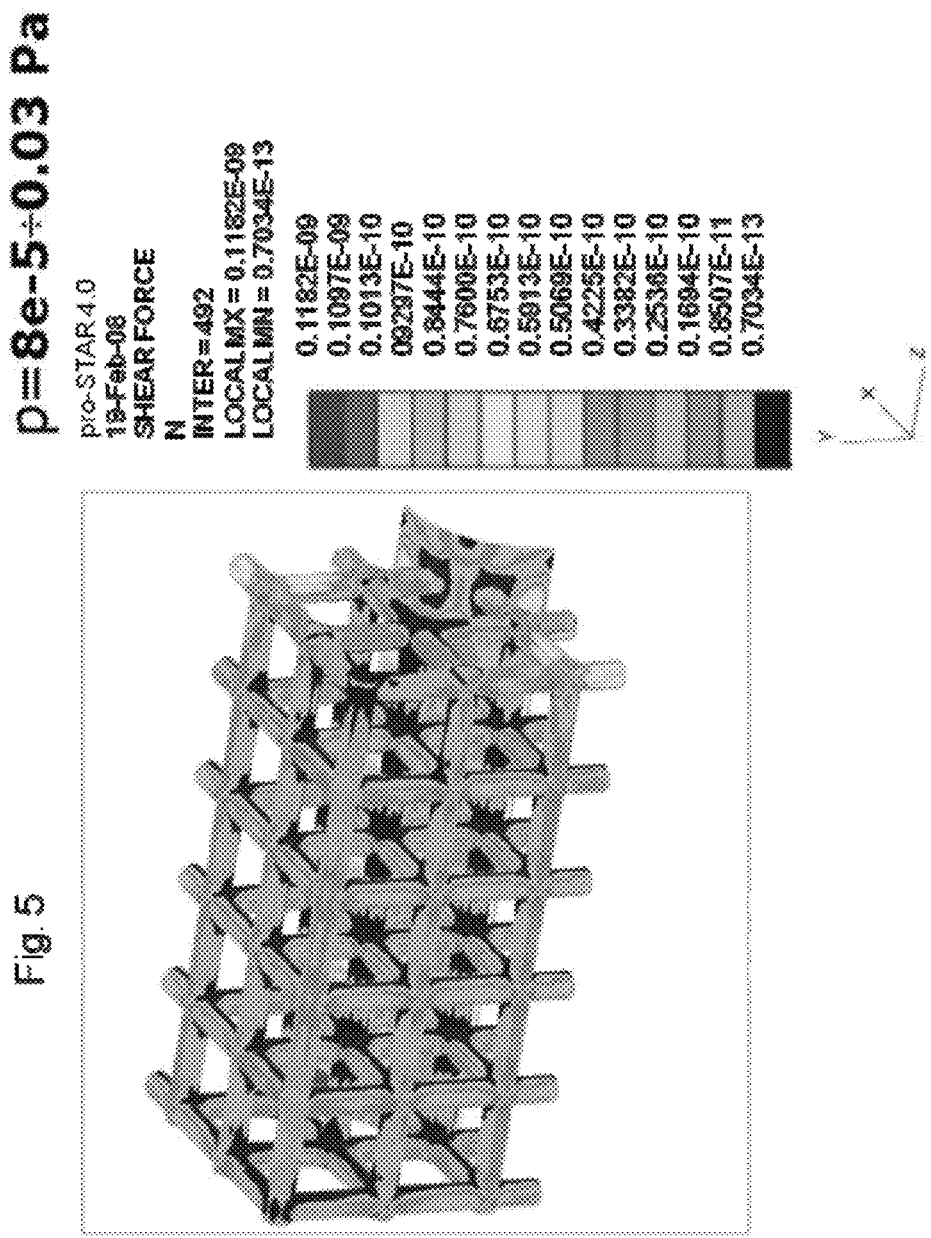

FIG. 5 illustrates an example of Computational Fluid Dynamics analysis, where the distribution of flow is throughout the structure.

Figure 6:
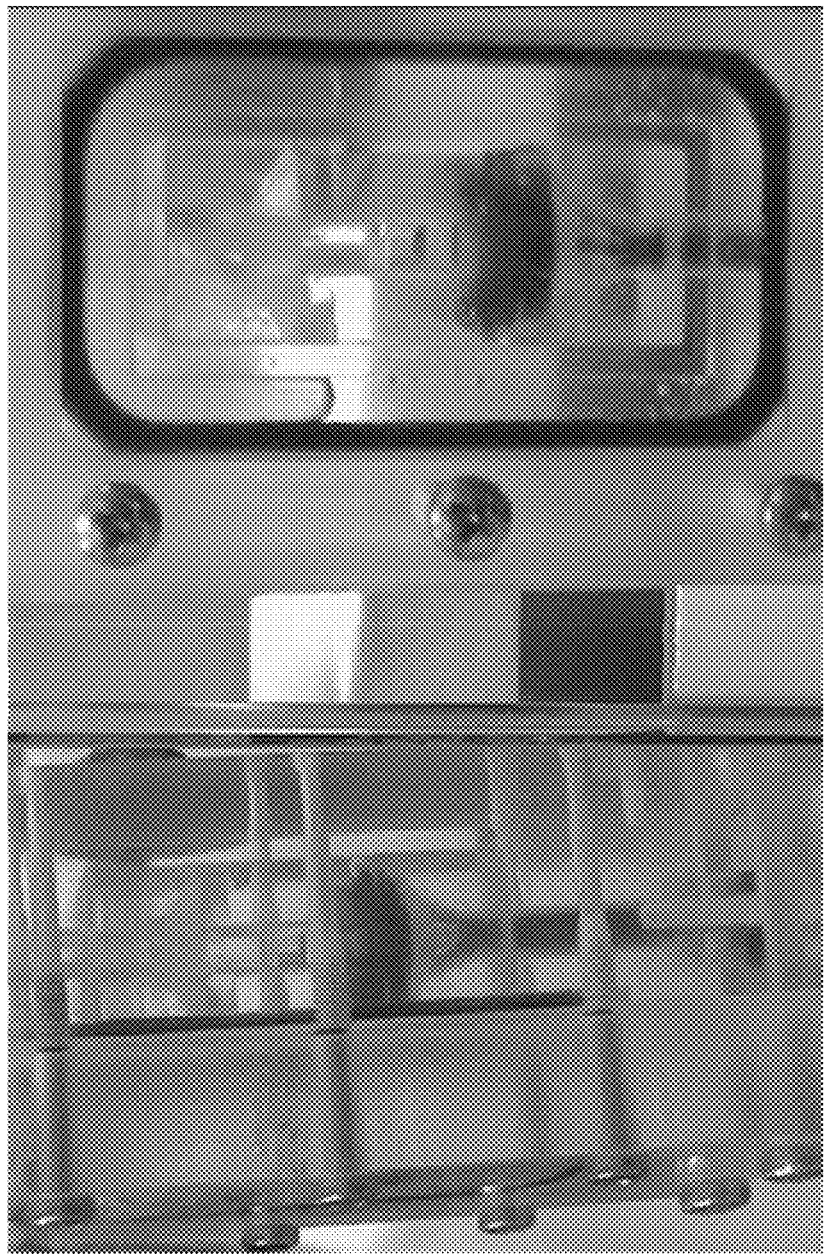

FIG. 6 is a photographic flow analysis.

Figure 7:
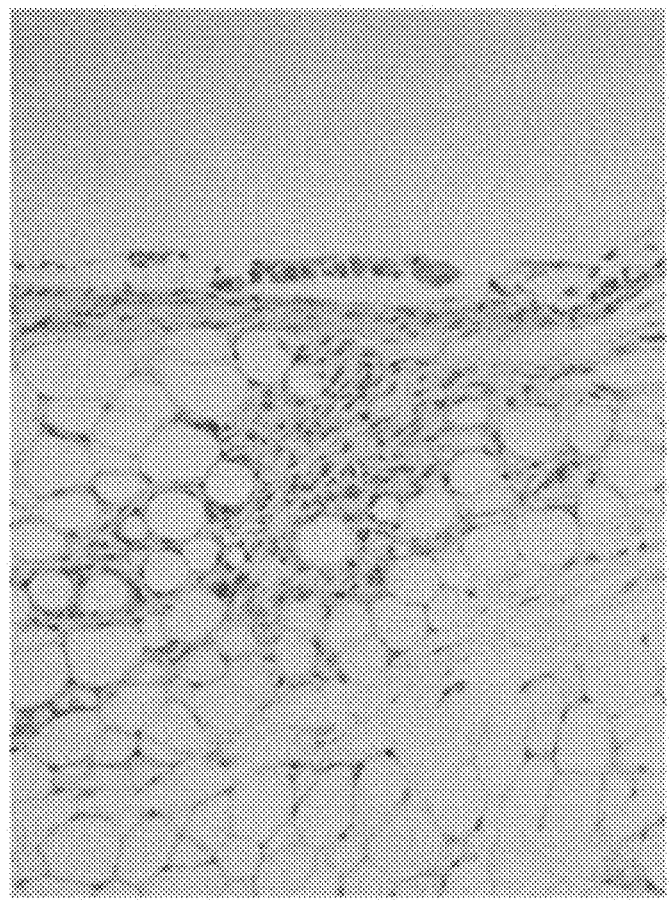
Figure 8:
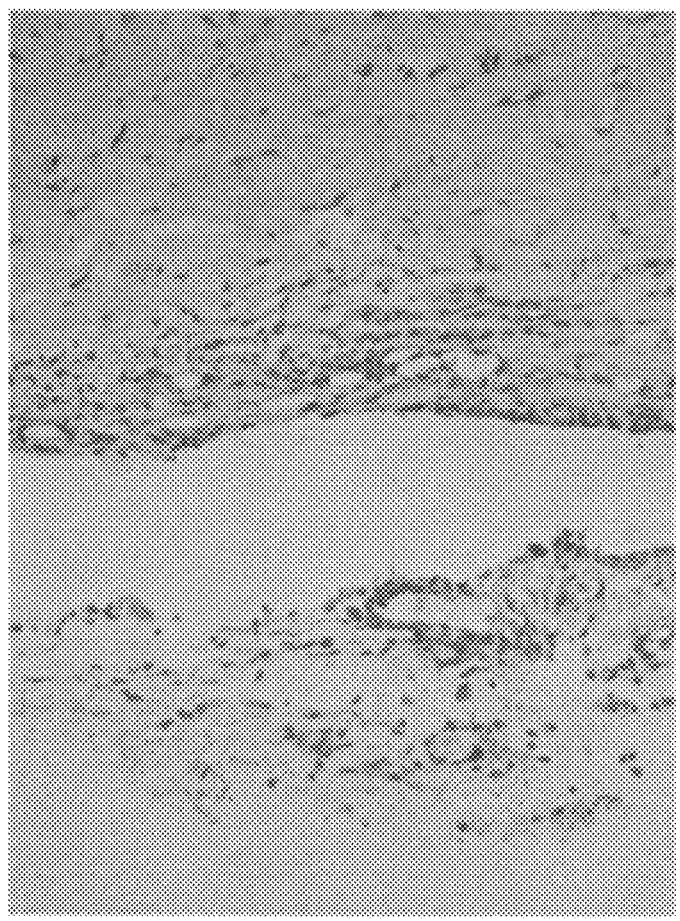

FIG. 7 and FIG. 8 illustrate the growth of cells and the absence of inflammatory process for the sample PD and the sample PDC respectively. Microphotographs are 20× of magnification and the cutis are on the top of the microphotographs.

FIG. 9 illustrates the areas of application and analysis of the samples HA, PD and PDC for the cells growth experiments on mice. The external analysis of the samples does not reveal any fibrotic reaction or inflammation process.

The invention claimed is:
1. A continuous bioreactor culturing device comprising:
   (a) a 3-dimensional lattice-shaped scaffold having x, y and z Cartesian axes thereby providing an overall shape to the scaffold, the scaffold formed by a matrix of layered, interconnected growth surfaces spaced in the x, y and z Cartesian axes at regular intervals thereby providing a plurality of interconnected open spaces all arranged orthogonally in a 3-dimensional matrix and parallel to the x, y and z Cartesian axes of the scaffold disposed between the spaced interconnected growth surfaces, the interconnected open spaces allowing a fluid to pass continuously through the scaffold parallel to and in the direction of at least one of the x, y and z Cartesian axes, the scaffold including a first cylindrical support on a first side of the scaffold that couples with a bioreactor fluid inlet and a second cylindrical support on a second side of the scaffold that couples with a bioreactor fluid outlet allowing the first side to serve as an inlet for the fluid and the second side to serve as an outlet for the fluid as the fluid passes through the scaffold, and
   (b) fluid distribution means, including the bioreactor fluid inlet and the bioreactor fluid outlet, disposed at the inlet and at the outlet of the scaffold, respectively, where the bioreactor fluid inlet includes multiple inlet distribution conduits that collectively and continuously distribute the fluid through and around the open spaces of the first side and the bioreactor fluid outlet includes multiple outlet conduits that collectively and continuously collect the fluid from the second side;
wherein all of the interconnected growth surfaces are aligned with each other in relation to the x, y and z Cartesian axes, and the plurality of interconnected open spaces of the scaffold have a substantially cubic shape.

2. A device according to claim 1 wherein the scaffold is formed by the interconnected growth surfaces spaced at regular intervals around a central support that includes the first cylindrical support and the second cylindrical support at oppositely disposed ends of the central support.

3. A device according to claim 1 wherein the interconnected growth surfaces are defined by the interconnection of multiple fibers or three-dimensional structures.

4. A device according to claim 1 wherein the interconnected growth surfaces are spaced at regular intervals equal or larger than 0.9 mm and smaller than 3.0 mm.

5. A device according to claim 1 wherein the interconnected growth surfaces are spaced at regular intervals equal or larger than 1.0 mm and smaller than 3.0 mm.

6. A device according to claim 1 wherein the interconnected growth surfaces are spaced at regular intervals equal or larger than 1.0 mm and smaller than 2.0 mm.

7. A device according to claim 1 further comprising an aseptically sealed housing that can be disassembled at the completion of the culture period.

8. A device according to claim 7 wherein the aseptically sealed housing comprises a sealed removable cover, an inlet distribution means, and necessary support means required to locate and secure the growth surfaces in the culture device.

9. A device according to claim 8 wherein the aseptically sealed housing further comprises an exit distribution means.

10. A device according to claim 1 wherein the overall shape of the scaffold is a cubic shape.

11. A device according to claim 1, wherein all of the interconnected growth surfaces are spaced at regular intervals equal or larger than 0.7 mm and smaller than 3.0 mm.

12. A device according to claim 1, where the bioreactor fluid inlet and the bioreactor fluid out each have a central recess for coupling with the first cylindrical support and the second cylindrical support, respectfully.

13. A method of culturing bone cells for use in dental implants or bone reconstruction in a bioreactor, said method comprises:
   a) providing, in an environment suitable for cell growth, a continuous culturing device including a 3-dimensional lattice-shaped scaffold having x, y and z Cartesian axes thereby providing an overall shape to the scaffold, the scaffold formed by a matrix of layered, interconnected growth surfaces spaced in the x, y and z Cartesian axes at regular intervals thereby providing a plurality of interconnected open spaces all arranged orthogonally in a 3-dimensional matrix and parallel to the x, y and z Cartesian axes of the scaffold disposed between the spaced interconnected growth surfaces, the interconnected open spaces allowing a fluid to pass continuously through the scaffold parallel to and in the direction of at least one of the x, y and z Cartesian axes, the scaffold including a first cylindrical support on a first side of the scaffold that couples with a bioreactor fluid inlet and a second cylindrical support on a second side of the scaffold that couples with a bioreactor fluid outlet allowing the first side to serve as an inlet for the fluid and the second side to serve as an outlet for the fluid as the fluid passes through the scaffold, and fluid distribution means, including the bioreactor fluid inlet and the bioreactor fluid outlet, disposed at the inlet and at the outlet of the scaffold, respectively, where the bioreactor fluid inlet includes multiple inlet distribution conduits that collectively and continuously distribute the fluid through and around the open spaces of the first side and the bioreactor fluid outlet includes multiple outlet conduits that collectively and continuously collect the fluid from the second side,
   wherein all of the interconnected growth surfaces are aligned with each other in relation to the x, y and z Cartesian axes and the plurality of interconnected open spaces of the scaffold have a substantially cubic shape;
   b) seeding the continuous culturing device with bone cells; and
   c) growing the bone cells for a sufficient amount of time for cultivation of said bone cells.

14. A method according to claim 13 which further comprises d) harvesting the grown bone cells.

15. A method according to claim 13, wherein all of the interconnected growth surfaces are spaced at regular intervals equal or larger than 12.7 mm and smaller than 3.0 mm.

16. A method according to claim 13, wherein the here the bioreactor fluid inlet and the bioreactor fluid out each have a central recess for coupling with the first cylindrical support and the second cylindrical support, respectfully.

\* \* \* \* \*